US00PP10273P

United States Patent [19]

Zary

[11] Patent Number: Plant 10,273

[45] Date of Patent: Mar. 10, 1998

[54] HYBRID TEA ROSE PLANT NAMED 'JACLION'

[75] Inventor: Keith W. Zary, Thousand Oaks, Calif.

[73] Assignee: Bear Creek Gardens, Inc., Medford, Oreg.

[21] Appl. No.: 759,937

[22] Filed: Dec. 3, 1996

[51] Int. Cl.[6] ..... A01H 5/00

[52] U.S. Cl. ..... Plt./11

[58] Field of Search ..... Plt./11, 14, 16

[56] References Cited

U.S. PATENT DOCUMENTS

P.P. 9,718 12/1996 Fryer ..... Plt./11

*Primary Examiner*—Howard J. Locker

*Attorney, Agent, or Firm*—Klarquist Sparkman Campbell Leigh & Whinston, LLP

[57] ABSTRACT

A new and distinct variety of rose plant of the hybrid tea class, having a vigorous, upright, branching growth habit; formal, hybrid tea-shaped flowers in attractive pastel shades; glossy, dark green, leathery foliage; resistance to powdery mildew and rust; and very pleasant light-to-moderate scent.

1 Drawing Sheet

The present invention relates to a new and distinct variety of rose plant of the hybrid tea class which was originated by me by crossing the variety JACara, U.S. Plant Pat. No. 6,316, with the variety Medallion, U.S. Plant Pat. No. 2,997.

The primary objective of this breeding was to produce a new rose variety having the vigorous habit, clean foliage and heavy flower production of the female hybrid tea parent combined with the extremely large flower of the male parent. The objective was substantially achieved, along with other desirable improvements, as evidenced by the following unique combination of characteristics that are outstanding in the new variety and that distinguish it from its parents, as well as from all other varieties of which I am aware:

1. Vigorous, upright branching plant;
2. Formal, classic hybrid tea-shaped flower in attractive pastel shades;
3. Glossy, dark green, leathery foliage;
4. Resistance to powdery mildew and rust; and
5. Very pleasant, light-to-moderate scent.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—JACara, U.S. Plant Pat. No. 6,316.

*Pollen parent.*—Medallion, U.S. Plant Pat. 2,997.

Classification:

*Botanical.*—*Rosa hybrida.*

*Commercial.*—Hybrid tea.

FLOWER

Observations made January through September, 1996 from specimens grown in a garden environment at Somis, Calif.

Blooming habit: Recurrent.

Bud:

*Size.*—1¾ inches to 2 inches long when the petals start to unfurl.

*Form.*—The bud form is long, pointed ovoid.

*Color.*—When sepals first divide, bud color is Yellow-White Group 158A edged at the tip of the bud in Red Group 43C to 43D. When half blown, the upper sides of the petals are Red Group 43D at the edges, Yellow-White Group 158C in the middle and Yellow-White Group 158A near the base; and the lower sides of the petals are Yellow-White Group 158A.

*Sepals.*—Color: Green Group 138A. Surface texture: Covered in fine hairs. There are three lightly appendaged sepals. There are two unappendaged sepals with hairy edges.

*Receptacle.*—Color: Green Group 137D with some bronze coloration when touched by the sun. Shape: Funnel. Size: Large (⅝ inch × ½ inch). Surface: Smooth.

*Peduncle.*—Length: Medium (3 inches). Surface: Smooth. Color: Bronzy. Strength: Stiff, erect.

Bloom:

*Size.*—Large. Average open size is 5 to 6 inches.

*Borne.*—Singly.

*Stems.*—Medium. Average length is about 14 to 18 inches.

*Form.*—When first open: High centered. Permanence: Outer petals curl back.

*Petalage.*—Number of petals under normal conditions: 30 to 35.

*Color.*—The upper side of the petals is Yellow-White Group 158A at the base, Yellow-White Group 158C in the center, and Red Group 43D at the edge. The reverse side of the petals is Yellow-White Group 158A. The base of each petal has a small yellow (Yellow Group 10C) half moon at the point of attachment. The major color on the upper side is Yellow-White Group 158A.

*Variegations.*—None.

*Discoloration.*—The general tonality at the end of the first day: No change. At the end of the third day: Gradual change in color to more and more Red Group 43D. This change continues through to petal drop at day six or seven.

*Fragrance.*—Moderate.

Petals:

*Texture.*—Thick.

*Shape.*—Round.

*Form.*—Tips slightly recurved, edges slightly quilled.

*Arrangement.*—Imbricated, with few petaloids in the center.

*Persistence.*—Drop off cleanly.

*Lastingness.*—On the plant: Fair (6 to 7 days). As a cut flower: Fair (7 to 8 days).

Reproductive parts:

*Anthers.*—Size: Large. Quantity: Many. Color: Yellow. Arrangement: Regular around styles.

*Filaments.*—Color: Yellow.

*Pollen.*—Color: Gold yellow.

*Styles.*—Color: Red.

*Stigmas.*—Greenish white.

Form: Bush.

Growth: Vigorous, upright, branching. (Height in California after one year of growth is 5 feet.)

Foliage: Number of leaflets on normal mid-stem leaves: 5.

*Size.*—Large (5½ to 6 inches × 5 inches).

*Quantity.*—Abundant.

*Color.*—New foliage: Greyed Red Group 178A for both surfaces. Old foliage: Green Group 136B for the upper surface Green Group 136C for the lower surface.

Leaflets:

*Shape.*—Pointed oval.

*Texture.*—Upper side: Leathery, glossy.

*Edge.*—Serrated.

*Serration.*—Single, small.

*Petiole rachis.*—Color: Reddish.

*Petiole underside.*—Smooth, with occasional prickles.

*Stipules.*—Medium (½ inch), serrated.

*Disease resistance.*—Resistant to mildew and rust under normal growing conditions at Somis, Calif.

Wood:

*New wood.*—Color: Light green. Bark: Smooth.

*Old wood.*—Color: Green. Bark: Smooth.

Prickles:

*Quantity.*—On main canes from base: Ordinary. On laterals from main canes: Ordinary.

*Form.*—Medium (⅜ inch), hooked downward.

*Color when young.*—Red.

Small Prickles:

*Quantity.*—On main stalks: None. On laterals: None.

I claim:

1. A new and distinct variety of rose plant of the hybrid tea class, substantially as herein shown and described, characterized particularly as to novelty by the unique combination of its vigorous, upright branching growth habit; its formal, hybrid tea-shaped flower in attractive pastel shades; its glossy, dark green, leathery foliage; its resistance to powdery mildew and rust; and its very pleasant, light-to-moderate scent.

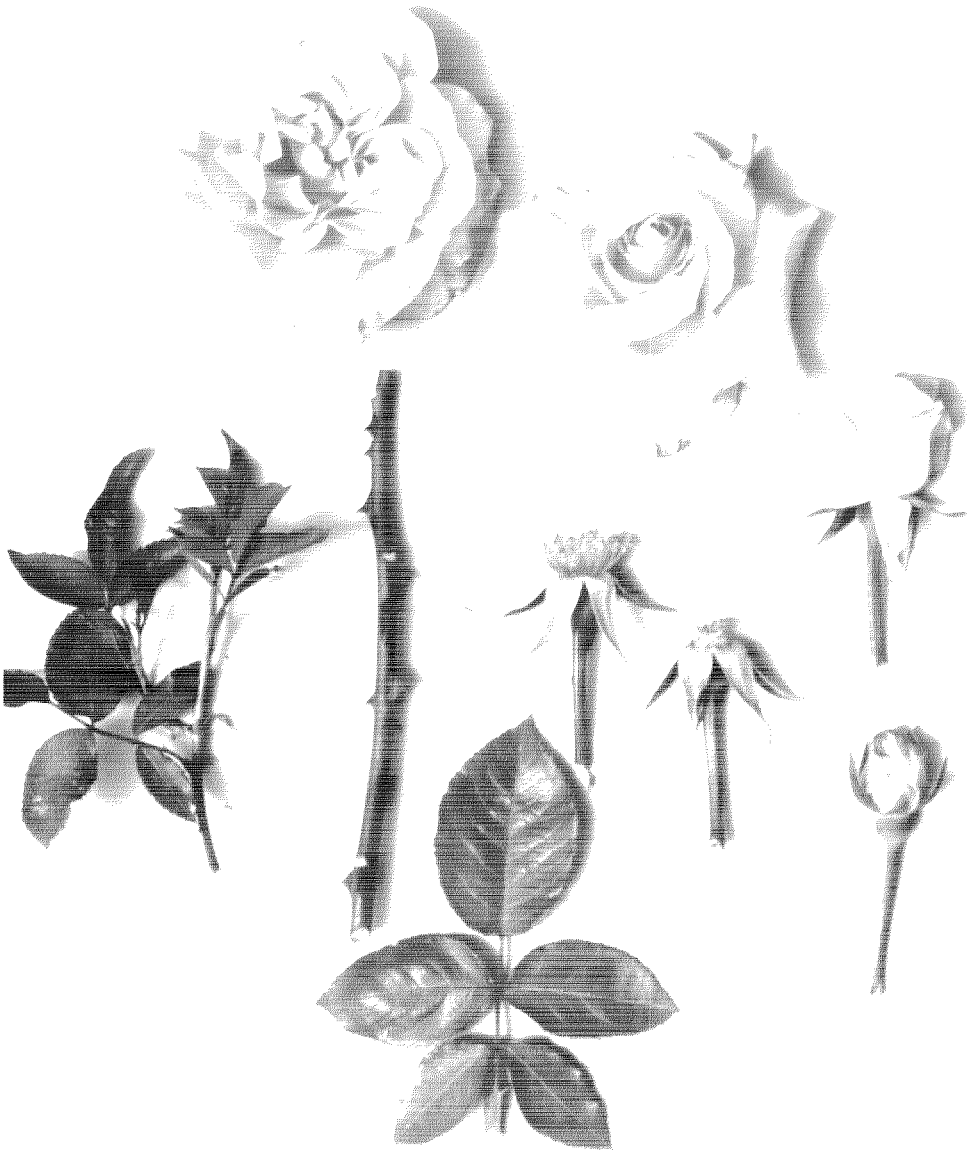

* * * * *